(12) United States Patent
Morita

(10) Patent No.: US 11,414,693 B2
(45) Date of Patent: Aug. 16, 2022

(54) PHOSPHATIDYLINOSITOL QUANTIFICATION METHOD AND QUANTIFICATION KIT

(71) Applicant: NATIONAL UNIVERSITY CORPORATION SHIGA UNIVERSITY OF MEDICAL SCIENCE, Otsu (JP)

(72) Inventor: Shin-Ya Morita, Otsu (JP)

(73) Assignee: NATIONAL UNIVERSITY CORPORATION SHIGA UNIVERSITY OF MEDICAL SCIENCE, Otsu (JP)

(*) Notice: Subject to any disclaimer, the term of this patent is extended or adjusted under 35 U.S.C. 154(b) by 246 days.

(21) Appl. No.: 16/615,705

(22) PCT Filed: May 24, 2018

(86) PCT No.: PCT/JP2018/020027
§ 371 (c)(1),
(2) Date: Nov. 21, 2019

(87) PCT Pub. No.: WO2018/216776
PCT Pub. Date: Nov. 29, 2018

(65) Prior Publication Data
US 2020/0181676 A1    Jun. 11, 2020

(30) Foreign Application Priority Data
May 25, 2017    (JP) .............................. JP2017-103714

(51) Int. Cl.
*C12Q 1/44* (2006.01)
*C12Q 1/28* (2006.01)
*C12Q 1/32* (2006.01)
*G01N 21/76* (2006.01)

(52) U.S. Cl.
CPC ................ *C12Q 1/44* (2013.01); *C12Q 1/28* (2013.01); *C12Q 1/32* (2013.01); *G01N 21/76* (2013.01)

(58) Field of Classification Search
CPC ... C12Q 1/44; C12Q 1/28; C12Q 1/32; G01N 21/76
See application file for complete search history.

(56) References Cited

U.S. PATENT DOCUMENTS

2017/0114387 A1    4/2017    Morita

FOREIGN PATENT DOCUMENTS

| EP | 0477001 B1 * | 6/1996 | |
| JP | 2001-190299 A | 7/2001 | |
| JP | 2008143835 A * | 6/2008 | |
| JP | 2013-255436 A | 12/2013 | |
| JP | 5800830 B2 * | 10/2015 | ............... C12Q 1/26 |
| NO | 2012/070617 A1 | 5/2012 | |
| WO | 2015/151801 A1 | 10/2015 | |
| WO | WO-2015151801 A1 * | 10/2015 | ............... C12Q 1/26 |

OTHER PUBLICATIONS

English machine translation of Koga et al., JP 2008-143835 A, 2008.*
Marty-Teysset, C., De La Torre, F., & Garel, J. R. (2000). Increased production of hydrogen peroxide by *Lactobacillus delbrueckii* subsp. *bulgaricus* upon aeration: involvement of an NADH oxidase in oxidative stress. Applied and environmental microbiology, 66(1), 262-267 (Year: 2000).*
Koga JP-2008143835-A translation (Year: 2008).*
Morita WO-2012070617-A1 translation (Year: 2012).*
Van Straaten, K. E., Zheng, H., Palmer, D. R., & Sanders, D. A. (2010). Structural investigation of myo-inositol dehydrogenase from *Bacillus subtilis*: implications for catalytic mechanism and inositol dehydrogenase subfamily classification. Biochemical Journal, 432(2), 237-247 (Year: 2010).*
Yang, H., & Roberts, M. F. (2003). Phosphohydrolase and transphosphatidylation reactions of two Streptomyces phospholipase D enzymes: covalent versus noncovalent catalysis. Protein science, 12(9), 2087-2098. (Year: 2003).*
Morita WO 2015/151801 A1 translation (Year: 2015).*
International Search Report dated Aug. 21, 2018 from International Application No. PCT/JP2018/020027, 4 pages, including English translation.
Saito et al., "Microdetermination by enzyme method of phosphatidylinositol (PI), and measurement of ratio of PG/PI in amniotic fluid", Journal of Japanese Medical Society for Biological Interface, 1989, vol. 20, pp. 82-84.
Batchelor et al., "A Resorufin-Based Fluorescent Assay for Quantifying NADH", Analytical Biochemistry, 2002, vol. 305, No. 1, pp. 118-119.

* cited by examiner

*Primary Examiner* — Louise W Humphrey
*Assistant Examiner* — Trevor Logan Kane
(74) *Attorney, Agent, or Firm* — MH2 Technology Law Group, LLP

(57) ABSTRACT

Disclosed is a method for quantifying phosphatidylinositol in a sample, comprising the following step: (1) treating the sample with phospholipase D and inositol dehydrogenase; and a kit for quantifying phosphatidylinositol, containing phospholipase D and inositol dehydrogenase.

15 Claims, 3 Drawing Sheets

PHOSPHATIDYLINOSITOL QUANTIFICATION METHOD AND QUANTIFICATION KIT

CROSS-REFERENCE TO RELATED APPLICATIONS

This application is a U.S. National Stage application of PCT/JP2018/020027 filed 24 May 2018, which claims priority to Japanese Application No. 2017-103714 filed 25 May 2017, the entire disclosures of which are incorporated herein by reference.

TECHNICAL FIELD

The present invention relates to a method for quantifying phosphatidylinositol, and a kit for quantifying phosphatidylinositol.

BACKGROUND ART

Phosphatidylinositol (PI), a type of phospholipid, has a structure in which two fatty acids and inositol phosphate are attached to a glycerol backbone. In mammalian cells, PI is present in the cellular plasma membrane and in the intracellular membrane including the endoplasmic reticulum membrane and Golgi apparatus; PI accounts for 5% to 10% of intracellular phospholipids. In addition to its structural roles of forming cell membranes, it has recently become increasingly clear that PI plays extremely important roles in intracellular signaling by modulating the activities and localization of various membrane proteins (channels, transporters, receptors, enzymes, etc.).

Conventionally, PI has been quantified by a combination method of thin-layer chromatography (TLC) and phosphorus quantification. However, this method exhibits low detection sensitivity and low quantification accuracy, requiring time and effort. Accurate quantification requires skilled techniques, since the spots on the TLC obtained by various coloring methods must be carefully scraped with a spatula for phosphorus quantification etc.

In high-performance liquid chromatography (HPLC) analysis, PI is quantified by detecting acyl chain double bonds in the molecules by ultraviolet absorption; this method is thus significantly affected by the type of fatty-acid chains. Particularly, a molecular species of PI that consists of saturated fatty-acid chains would not be detected. Further, a molecular species with polyunsaturated acyl chains would show a large peak, leading to be poor quantitative.

In mass spectrometry (MS) analysis, detection is performed for each molecular species with different types of fatty-acid chains of PI; thus, quantification of PI is difficult. For example, in the case of PI in mammalian cells, 50 or more different molecular species exist with different combinations of two acyl chains. In MS analysis, each molecular species shows a peak with a different ionization efficiency.

PI is an essential and indispensable component that has a wide variety of functions in organisms. Although PI has been very actively studied worldwide, analytical methods for PI are still extremely poor. Therefore, the role of PI in blood and the association of PI with diseases have not yet been understood.

The present inventor has previously developed enzymatic fluorometric quantification methods of phospholipids (phosphatidylcholine, phosphatidylethanolamine, phosphatidic acid, phosphatidylserine, sphingomyelin, and cardiolipin) (e.g., Patent Literature (PTL) 1, PTL 2, and PTL 3).

PTL 1 reports an enzymatic quantification method of phosphatidylserine in which the fluorescence intensity of a compound produced by treating a sample with phospholipase D, L-amino-acid oxidase, and peroxidase is measured.

PTL 2 reports an enzymatic quantification method of sphingomyelin in which the fluorescence intensity of a compound produced by treating a sample with sphingomyelinase, alkaline phosphatase, choline oxidase, and peroxidase is measured.

Further, PTL 3 reports an enzymatic quantification method of cardiolipin in which the fluorescence intensity of a compound produced by treating a sample with phospholipase D, glycerol kinase, glycerol-3-phosphate oxidase, and peroxidase is measured.

However, since an enzymatic fluorometric quantification method of PI has not yet been developed, an inability to determine the profile of all phospholipid classes by excluding PI is problematic.

CITATION LIST

Patent Literature

PTL 1: WO2012/070617
PTL 2: JP2013-255436A
PTL 3: WO2015/151801

SUMMARY OF INVENTION

Technical Problem

As stated above, PI is conventionally quantified by thin-layer chromatography/phosphorous quantification methods. However, these methods have disadvantages in that the detection sensitivity and quantification accuracy are low, and time and effort are required.

An objective of the present invention is to provide a method for quantifying phosphatidylinositol conveniently with high sensitivity, and a kit for quantifying phosphatidylinositol.

Solution to Problem

The present inventor conducted extensive research to achieve the above objective, and found that the above objective can be achieved by using a series of enzyme reactions shown in FIG. 1. The method for quantifying phosphatidylinositol shown in FIG. 1 is described below.
(i) PI is hydrolyzed by phospholipase D to produce inositol and phosphatidic acid (PA).
(ii) Inositol is reacted with $NAD^+$ by inositol dehydrogenase to produce NADH.
(iii) NADH is oxidized with NADH oxidase to produce $H_2O_2$.
(iv) 10-Acetyl-3,7-dihydroxyphenoxazine (Amplex (tradename) Red) is reacted with $H_2O_2$ by peroxidase to produce resorufin. The PI content can be measured by measuring the fluorescence intensity of resorufin.

Based on these findings, the present invention has been accomplished as a result of further research. The present invention provides the following method and kit for quantifying phosphatidylinositol.
(I) Method for Quantifying Phosphatidylinositol
(I-1) A method for quantifying phosphatidylinositol in a sample, comprising the step of:
(1) treating the sample with phospholipase D and inositol dehydrogenase.

(I-2) The method according to (I-1), wherein the sample is further treated with NADH oxidase and peroxidase in step (1).
(I-3) The method according to (I-1) or (I-2), further comprising the step of:
(2) measuring the fluorescence intensity, absorbance, or luminescence intensity of a compound generated in step (1) to quantify phosphatidylinositol using a calibration curve obtained beforehand.
(I-4) The method according to any one of (I-1) to (I-3), wherein in step (1), heat treatment is performed at 60° C. or higher after the treatment with phospholipase D, and the treatment with inositol dehydrogenase is then performed.
(I-5) The method according to any one of (I-1) to (I-4), wherein the series of enzyme treatments is performed at a neutral pH range.
(II) Kit for Quantifying Phosphatidylinositol
(II-1) A kit for quantifying phosphatidylinositol containing phospholipase D and inositol dehydrogenase.
(II-2) The kit according to (II-1), further containing NADH oxidase and peroxidase.

Advantageous Effects of Invention

The present invention, method and kit for quantifying phosphatidylinositol, can quantify phosphatidylinositol with high sensitivity and high accuracy.
The detection limit of the present invention is 10 pmol, which is extremely highly sensitive compared to conventional PI quantification methods. This enables highly accurate quantification.
Further, the main necessary procedure of the present invention is pipetting of samples and reaction solutions into a microplate, which is very simple. This enables high-throughput quantification.

DESCRIPTION OF EMBODIMENTS

Figure 1:
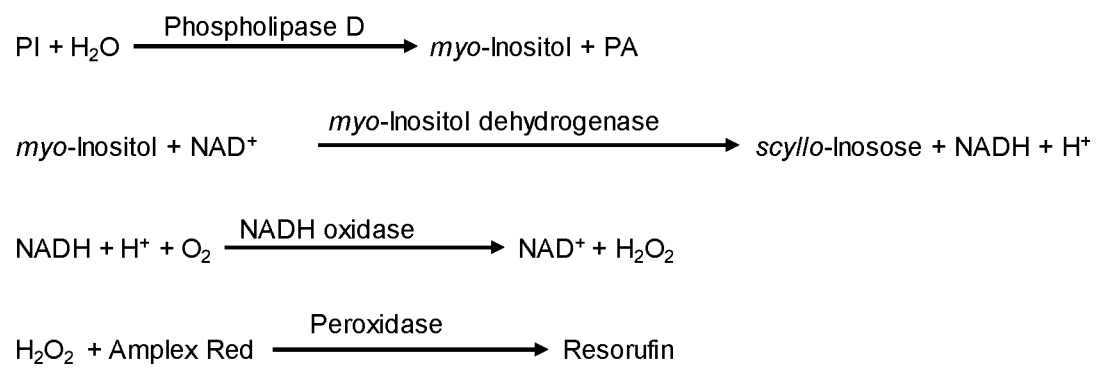
FIG. 1 shows reactions in the PI quantification method of the present invention.

The present invention, method and kit for quantifying phosphatidylinositol, is described in detail below.

Method for Quantifying Phosphatidylinositol
The method for quantifying PI in a sample according to the present invention comprises the following step:
(1) treating the sample with phospholipase D and inositol dehydrogenase.
The method for quantifying PI in a sample according to the present invention may further comprise the following step:
(2) measuring the fluorescence intensity, absorbance, or luminescence intensity of a compound generated in step (1) to quantify phosphatidylinositol using a calibration curve obtained beforehand.
Examples of PI detectable by the method for quantifying PI according to the present invention include PI in which the inositol moiety is myo-inositol; phosphorylated phosphatidylinositol (PIP), such as phosphatidylinositol monophosphate (e.g., those in which inositol is phosphorylated at position 4 or 5); and the like.
Each step is described below.
Step (1)
In step (1), a sample is treated with phospholipase D and inositol dehydrogenase. The sample is preferably further treated with NADH oxidase and peroxidase.
By treating the sample with phospholipase D, inositol and PA are produced from PI and $H_2O$. Subsequently, by treating the resulting product with inositol dehydrogenase, inosose, NADH, and $H^+$ are produced from inositol and $NAD^+$ (nicotinamide adenine dinucleotide). Then, by treating the resulting product with NADH oxidase, $NAD^+$ and $H_2O_2$ are produced from NADH, $H^+$, and $O_2$.
Phospholipase D (EC 3.1.4.4) is a phospholipid hydrolase that hydrolyzes the phosphodiester linkage of a glycerophospholipid at the base side. As the phospholipase D used in the present invention, phospholipase D derived from microorganisms, animals, and plants can be widely used, as long as it hydrolyzes phosphatidylinositol to produce inositol and phosphatidic acid. Of these, phospholipase D derived from microorganisms is preferable, phospholipase D derived from the genus *Streptomyces* is more preferable, and phospholipase D derived from *Streptomyces chromofuscus* is particularly preferable.
As the inositol dehydrogenase (inositol-2-dehydrogenase) (EC 1.1.1.18) used in the present invention, inositol dehydrogenase derived from microorganisms, animals, and plants can be widely used, as long as it can produce inosose, NADH, and $H^+$ from inositol (in particular, myo-inositol) and $NAD^+$. Of these, inositol dehydrogenase derived from microorganisms is preferable, and inositol dehydrogenase derived from *Bacillus subtilis* is particularly preferable.
As the NADH oxidase (EC 1.6.3.1) used in the present invention, NADH oxidase derived from microorganisms, animals, and plants can be widely used, as long as it can produce $NAD^+$ and $H_2O_2$ from NADH, $H^+$, and $O_2$. Of these, NADH oxidase derived from microorganisms is preferable, and NADH oxidase derived from *Bacillus licheniformis* is particularly preferable.
As the peroxidase (EC 1.11.1.7) used in the present invention, peroxidase derived from microorganisms, animals and plants can be widely used. Of these, peroxidase derived from plants is preferable, and peroxidase derived from horseradish is particularly preferable.
In the method for quantifying PI according to the present invention, to treat a sample with the above-described two or four enzymes, the two or four enzymes may be added at the same time for the reactions to occur concomitantly, or may be added sequentially for the reactions. However, the sample is preferably treated with enzymes in two separate steps: (a)

phospholipase D and inositol dehydrogenase; and (b) NADH oxidase and peroxidase. The sample is more preferably treated with enzymes in three separate steps: (a1) phospholipase D, (a2) inositol dehydrogenase, and (b) NADH oxidase and peroxidase. Reacting the sample with the two or four enzymes in such steps improves the accuracy.

The conditions in which a sample is treated with phospholipase D can be suitably determined according to the properties of the enzyme to be used. The pH is generally 6 to 9, and the temperature is generally 15 to 40° C. The time for which the sample is treated with phospholipase D can be suitably determined according to the properties of the sample to be analyzed; it is generally one minute or more.

The conditions in which a sample is treated with inositol dehydrogenase can be suitably determined according to the properties of the enzyme to be used. The pH is generally 6 to 12, and the temperature is generally 15 to 40° C. The time for which the sample is treated with inositol dehydrogenase can be suitably determined according to the properties of the sample to be analyzed; it is generally one minute or more.

The conditions in which a sample is treated with NADH oxidase can be suitably determined according to the properties of the enzyme to be used. The pH is generally 6 to 9, and the temperature is generally 15 to 60° C. The time for which the sample is treated with NADH oxidase can be suitably determined according to the properties of the sample to be analyzed; it is generally one minute or more.

The conditions in which a sample is treated with peroxidase can be suitably determined according to the properties of the enzyme to be used. The pH is generally 6 to 9, and the temperature is generally 15 to 50° C. The time for which the sample is treated with peroxidase can be suitably determined according to the properties of the sample to be analyzed; it is generally one minute or more.

When the active temperature and pH of the two or four enzymes are the same, all of the enzyme reactions can be performed at the same time. When the active temperature and pH are different among enzymes, the required temperature and pH are sequentially adjusted in steps to perform reactions. In the method for quantifying PI according to the present invention, the series of enzyme treatments is preferably performed at a neutral pH range (preferably a constant pH of 6.0 to 8.0).

Depending on the sample used in the method for quantifying PI according to the present invention, it is preferred that heat treatment be performed at 60° C. or higher (preferably 70° C. or higher, 80° C. or higher, or 90° C. or higher, particularly 90 to 100° C.) after the treatment with phospholipase D, and that the treatment with inositol dehydrogenase then be performed. After heat treatment, it is desirable to perform centrifugation to use the supernatant in the following process. Such heat treatment improves quantification accuracy.

In the method for quantifying PI according to the present invention, the amounts of the two or four enzymes in the reaction solution in which a sample is treated with the two or four enzymes can be suitably adjusted to amounts appropriate for analysis considering the amount of PI contained etc. Since high accuracy is attained by completing the reactions of these two or four enzymes almost perfectly within the reaction time, it is preferable to use sufficient amounts of enzymes.

In the present invention, the reaction solution for treating a sample with peroxidase contains a compound that increases the fluorescence intensity, absorbance, or luminescence intensity by reacting with $H_2O_2$ in the presence of peroxidase. When the four enzymes are sequentially reacted, the compound may be contained at least in the reaction solution for reacting with peroxidase. Examples of the compound include 10-acetyl-3,7-dihydroxyphenoxazine (Amplex Red). The concentration of 10-acetyl-3,7-dihydroxyphenoxazine in the reaction solution can be suitably adjusted; it is generally 10 to 500 μM.

The reaction solution for treating a sample with phospholipase D, inositol dehydrogenase, NADH oxidase, and peroxidase may contain, in addition to the sample and enzymes, a buffer solution, metal salts, $NAD^+$, and the like. Examples of the buffer solution include tris-hydrochloric acid buffer solutions, potassium phosphate buffer solutions, glycine-hydrochloric acid buffer solutions, acetic acid buffer solutions, citrate buffer solutions, and the like. Examples of the metal salt include magnesium salt, potassium salt, calcium salt, sodium salt, and the like. The reaction solution for treating a sample with inositol dehydrogenase preferably contains $NAD^+$.

The sample used in the present invention is not particularly limited, as long as the quantification of PI is required. Examples of the sample include cultured cells; culture media; human or animal tissues, and body fluids including blood; plant tissues and plant fluids; fungi; bacteria and bacteria culture solution; medicines; foods; supplements; and the like. The sample may be diluted with diluent, and examples of the diluent include buffer solutions. Examples of the buffer solution are those described above. The sample may be pre-treated before enzyme reaction, for example, by heating etc.

Step (2)

In Step (2), the fluorescence intensity, absorbance, or luminescence intensity of a compound generated in Step (1) is measured to quantify phosphatidylinositol using a calibration curve obtained beforehand.

Since one $H_2O_2$ molecule is generated from one PI molecule as a result of a series of reactions, PI can be quantified by measuring the amount of $H_2O_2$.

Specific examples of the measurement method in Step (2) include a method for measuring absorbance using a compound (e.g., N,N'-bis(2-hydroxy-3-sulfopropyl)tolidine) that reacts with $H_2O_2$ by peroxidase to show a new absorption wavelength; a method for measuring absorbance using compounds that react with $H_2O_2$ by peroxidase to perform oxidative condensation and to show a new absorption wavelength (e.g., oxidative condensation of phenol and 4-aminoantipyrine); a method for measuring fluorescence intensity using a compound (e.g., 10-acetyl-3,7-dihydroxyphenoxazine) that reacts with $H_2O_2$ by peroxidase to newly produce fluorescence; and a method for measuring the intensity of luminescence using a compound (e.g., luminol) that reacts with $H_2O_2$ by peroxidase to newly produce luminescence.

Of the above methods, a method for measuring fluorescence intensity using a compound that reacts with $H_2O_2$ by peroxidase to newly produce fluorescence is preferable, and a method for measuring the fluorescence intensity of resorufin generated by reacting 10-acetyl-3,7-dihydroxyphenoxazine (Amplex Red) with $H_2O_2$ by peroxidase is particularly preferable. Resorufin is a fluorescent compound, and has a maximum excitation wavelength of 571 nm and a maximum emission wavelength of 585 nm. In contrast, 10-acetyl-3,7-dihydroxyphenoxazine is a non-fluorescent compound, and fluorescence is not generated even when it is irradiated by light with a wavelength of around 571 nm. Since one resorufin molecule is generated from one PI molecule as a result of a series of reactions, PI can be quantified by measuring the amount of resorufin. The amount of resorufin can be determined by measuring the fluorescence intensity using, for example, a fluorescence microplate reader, at an excitation wavelength of 544 nm and an emission wavelength of 590 nm.

In the present invention, examples of the enzymes derived from microorganisms, animals, or plants widely include enzymes produced from microorganisms, animals, or plants, and their mutants that are obtainable by substitution, addition, deletion, and/or insertion of one or more amino acids in the amino acid sequence of the enzyme, and that have native enzymatic activities.

The range of "one or more" mentioned above is not particularly limited; it is, for example, 1 to 50, preferably 1 to 25, more preferably 1 to 12, even more preferably 1 to 9, and particularly preferably 1 to 5. The technique for substituting, deleting, inserting, or adding one or more amino acids in a specific amino acid sequence is known.

The enzymes mentioned above are commercially available; or can be produced by obtaining the gene according to known gene sequence information, and making transformants. The produced enzyme can be purified by affinity chromatography, ion exchange chromatography, hydroxyapatite column chromatography, ammonium sulfate precipitation, etc.

The following is one example of the method for quantifying PI according to the present invention. First, the standard samples are prepared by adequately diluting solutions of known PI concentrations, and their fluorescence intensities are measured by the method according to the present invention to obtain a calibration curve in response to PI concentration. The fluorescence intensity of a sample with an unknown PI content is then measured using the present invention. The PI content can be determined using the calibration curve.

The method for quantifying phosphatidylinositol according to the present invention can quantify phosphatidylinositol with high sensitivity and high accuracy.

Kit for Quantifying Phosphatidylinositol

The kit for quantifying phosphatidylinositol according to the present invention contains phospholipase D and inositol dehydrogenase. The kit for quantifying phosphatidylinositol according to the present invention preferably further contains NADH oxidase and peroxidase.

By performing the method for quantifying PI using the kit for quantifying PI according to the present invention, phosphatidylinositol can be quantified with high sensitivity and high accuracy.

As a method using a kit for quantifying PI according to the present invention, the above-described method for quantifying PI can be used.

Phospholipase D, inositol dehydrogenase, NADH oxidase, and peroxidase are the same as those described above.

The kit for quantifying PI according to the present invention may contain phospholipase D, inositol dehydrogenase, NADH oxidase, and peroxidase as enzyme solutions or dry powders. The kit for quantifying PI according to the present invention may contain a compound that produces a compound with measurable fluorescence intensity, absorbance, or luminescence intensity by treatment with peroxidase in the presence of $H_2O_2$. The kit for quantifying PI according to the present invention may also contain a buffer, metal salts, $NAD^+$, etc.; and the kit preferably contains at least $NAD^+$. Examples of the buffer and metal salt include those described above. It is preferable that the buffer and metal salt are contained in the kit as aqueous solutions or powders.

EXAMPLES

The following Examples describe the present invention in further detail. However, the present invention is not limited thereto.

Material

The reagents used in the Examples are shown below.
Phospholipase D derived from *Streptomyces chromofuscus* (T-07, manufactured by Asahi Kasei Corporation)
myo-Inositol dehydrogenase derived from *Bacillus subtilis* (E-INDHBS, manufactured by Megazyme)
NADH oxidase derived from *Bacillus licheniformis* (manufactured by Sanyo Fine Co., Ltd.)
Peroxidase derived from horseradish root (46261003, manufactured by Oriental Yeast Co., Ltd.)
Amplex Red reagent (Invitrogen)
PI derived from bovine liver, PI derived from soybean, dioleoyl-PI, lyso-PI, PI(4)P, and PI(5)P (manufactured by Avanti Polar Lipids, Inc.)
Other chemicals used were of the highest grade.

Enzymatic Measurement of PI

Reagent I1 contained 100 U/mL phospholipase D, 25 U/mL inositol dehydrogenase, 10 mM $NAD^+$, 2.4 mM $CaCl_2$, 50 mM NaCl, and 50 mM Tris-HCl (pH 7.4). Reagent I2 contained 1 U/mL NADH oxidase, 6.25 U/mL peroxidase, 187.5 µM Amplex Red, 0.125 volume % Triton X-100, 50 mM NaCl, and 50 mM Tris-HCl (pH 7.4). The Amplex Red Stop reagent was purchased from Invitrogen. A PI standard solution was prepared by dissolving PI derived from bovine liver in a 1 volume % Triton X-100 aqueous solution.

A PI standard solution or a sample (10 µL) was added to reagent I1 (10 µL), and incubated for 120 minutes at 25° C. After incubation, reagent I2 (80 µL) was added. After incubation for 60 minutes at 45° C., the Amplex Red Stop reagent (20 µL) was added. The fluorescence intensity was measured using a fluorescence microplate reader (Infinite M200, Tecan), and the excitation wavelength and the emission wavelength were set at 544 nm and 590 nm, respectively.

Measurement of PI Content in Cells

HEK293 cells were cultured in DMEM containing 10% heat-inactivated FBS in a humidified incubator (5% $CO_2$) at 37° C. The cells were seeded in 100-mm dishes, and incubated at 37° C. for a few days. After incubation, the cells were chilled on ice, washed with cold PBS, and scraped. The cells were sonicated for disruption. The cellular lipids were extracted by the Folch method, and dissolved in 1 volume % Triton X-100 prepared just before use. PI in the lipid extract from the cells was measured by the following enzymatic quantification method.

Reagent I1' contained 200 U/mL phospholipase D, 2.4 mM $CaCl_2$, 50 mM NaCl, and 50 mM Tris-HCl (pH 7.4). Reagent I2' contained 25 U/mL inositol dehydrogenase, 10 mM $NAD^+$, 150 mM NaCl, and 150 mM Tris-HCl (pH 7.4). Reagent I3' contained 1 U/mL NADH oxidase, 6.25 U/mL peroxidase, 187.5 µM Amplex Red, 0.125 volume % Triton X-100, 50 mM NaCl, and 50 mM Tris-HCl (pH 7.4).

A sample (10 µL) was added to reagent I1' (10 µL), and incubated for 60 minutes at 37° C. After incubation, heat treatment was performed at 96° C. for 3 minutes, followed by centrifugation at 10,000 rpm at room temperature for 5 minutes. Reagent I2' (10 µL) was added to 10 µL of the supernatant. After incubation for 120 minutes at 25° C., reagent I3' (80 μL) was added. After incubation for 60 minutes at 45° C., the Amplex Red Stop reagent (20 μL) was added. The fluorescence intensity was measured using a fluorescence microplate reader (Infinite M200, Tecan), and the excitation wavelength and the emission wavelength were set at 544 nm and 590 nm, respectively.

Results

Test Example 1: PI Measurement

Figure 2:
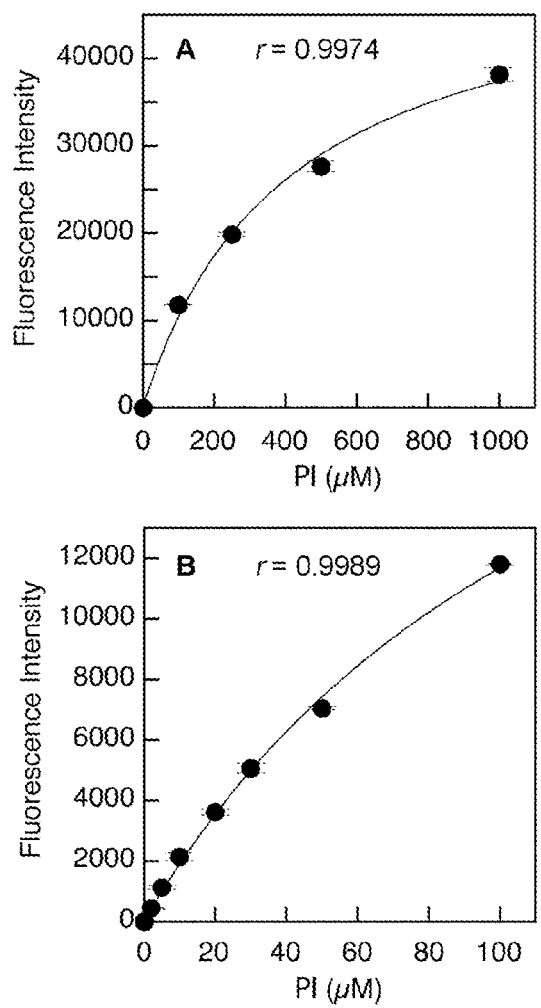
FIG. 2 shows graphs each showing a standard curve for PI measurement of Test Example 1. Each point represents the mean±S.D. of three measurements. The line was obtained by linear regression analysis. The correlation coefficients were r=0.9974 (A) and r=0.9989 (B).

A calibration curve was obtained by using PI standard solutions according to the enzymatic quantification method of PI described above (without heat treatment). The results are shown in FIG. 2.

The calibration curve for PI measurement was hyperbola between 0 to 1000 μM (r=0.9974: FIG. 2A, R=0.9989: FIG. 2B). The detection limit was 1 μM (10 pmol in the reaction solution).

Figure 3:
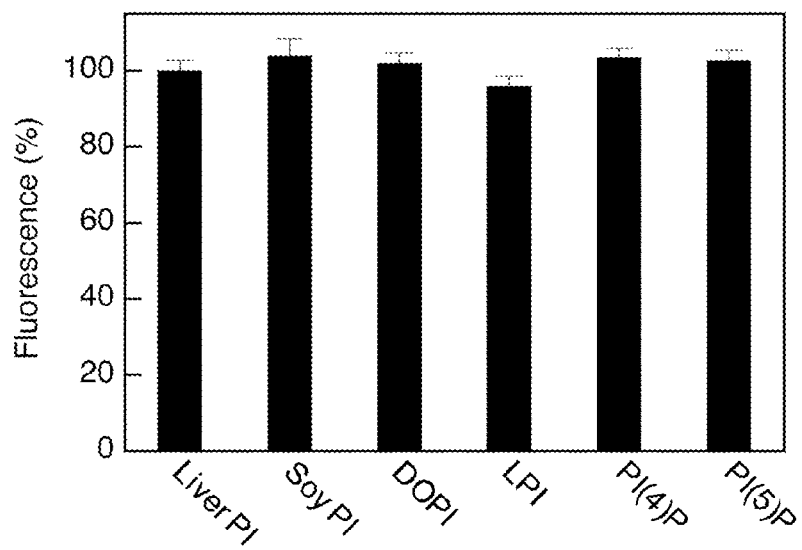
FIG. 3 is a graph showing fluorescence changes in response to PI derived from bovine liver (Liver PI), PI derived from soybean (Soy PI), dioleoyl-PI (DOPI), lyso-PI (LPI), and phosphatidylinositol monophosphate (PI(4)P (inositol is phosphorylated at position 4) and PI(5)P (inositol is phosphorylated at position 5)) (all 100 µM) in the PI measurement of Test Example 1. The fluorescence change in response to Liver PI is represented as 100%. Each bar represents the mean±S.D. of three measurements. Multiple comparison was performed using the Bonferroni test following ANOVA. There was no statistically significant difference among Liver PI, Soy PI, DOPI, LPI, PI(4)P, and PI(5)P.

The fluorescence intensities of six types of PIs were examined at the same concentration (100 μM) according to the enzymatic quantification method of PI described above (without heat treatment). FIG. 3 shows the results in which the fluorescence intensity in response to PI derived from bovine liver is represented as 100%. The comparison among three PIs, LPI, and two PIPs did not show a difference in fluorescence intensities at the same concentration.

Test Example 2: Measurement of PI in Cultured Cells

To confirm the accuracy of PI measurement, a known amount of PI was added to the cellular lipid extract to perform a recovery test (Table 1). As a result, almost 100% of the added PI was collected at each added amount. The results indicate that other cellular extracts do not interfere with the quantification of added PI, and that the quantification method according to the present invention is accurate.

TABLE 1

| Added amount of PI (μM) | Measured amount (μM) | Expected amount (μM) | Recovery rate (%) |
|---|---|---|---|
| 0 | 61.5 | | |
| 25 | 85.4 | 86.5 | 98.7 |
| 50 | 112.4 | 111.5 | 100.8 |
| 100 | 161.9 | 161.5 | 100.2 |
| 250 | 309.1 | 311.5 | 99.2 |

Figure 4:
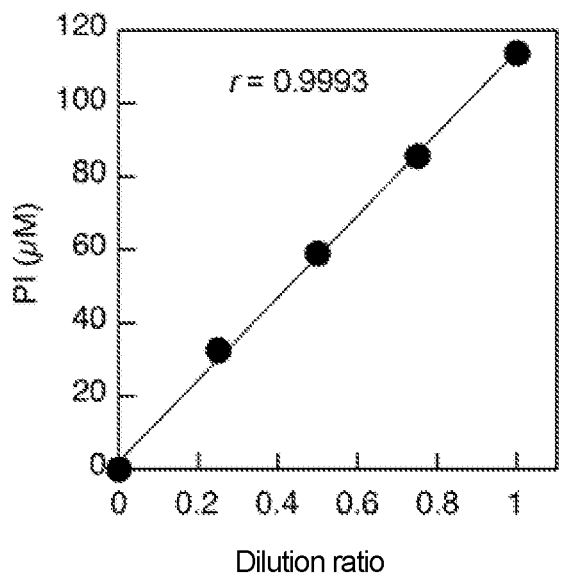
FIG. 4 is a graph showing the linearity of PI measurement in Test Example 2. The lipid extract from HEK293 cells was serially diluted with 1 volume % Triton (tradename) X-100. The correlation coefficient was r=0.9993.

To test the linearity of quantification, the lipid extract from HEK293 cells was serially diluted with a 1 volume % Triton X-100 aqueous solution. As shown in FIG. 4, a well-fitted regression line was obtained (r=0.9993).

The above results indicate that the method for quantifying PI according to the present invention has high specificity, high sensitivity, and high accuracy.

The invention claimed is:

1. A method for quantifying phosphatidylinositol in a sample, comprising the step of:
   (1) treating the sample with phospholipase D, inositol dehydrogenase, NADH oxidase, and peroxidase, wherein treatment of the sample with peroxidase is performed in a reaction solution comprising at least one compound that increases fluorescence intensity, absorbance, or luminescence intensity by reacting with $H_2O_2$ in the presence of peroxidase; and
   (2) measuring the fluorescence intensity, absorbance, or luminescence intensity generated in step (1) to quantify phosphatidylinositol in the sample using a calibration curve obtained beforehand.

2. The method according to claim 1, wherein in step (1), heat treatment is performed at 60° C. or higher after the treatment with phospholipase D, and the treatment with inositol dehydrogenase is then performed.

3. The method according to claim 1, wherein step (1) is performed at a neutral pH range.

4. A kit for quantifying phosphatidylinositol containing phospholipase D, inositol dehydrogenase, NADH oxidase, peroxidase, and a compound that produces a compound with measurable fluorescence intensity, absorbance, or luminescence intensity by treatment with peroxidase in the presence of $H_2O_2$.

5. The method of claim 1, wherein the sample is treated with phospholipase D and inositol dehydrogenase in a first reaction solution followed by treatment with NADH oxidase and peroxidase in a second reaction solution.

6. The method of claim 1, wherein the sample is treated with phospholipase D in a first reaction solution, followed by treatment with inositol dehydrogenase in a second reaction solution, and followed by treatment with NADH oxidase and peroxidase in a third reaction solution.

7. The method of claim 1, wherein the sample is treated with phospholipase D, inositol dehydrogenase, NADH oxidase, and peroxidase concomitantly.

8. The method of claim 1, wherein the at least one compound comprises N,N'-bis(2-hydroxy-3-sulfopropyl)tolidine, 10-acetyl-3,7-dihydroxyphenoxazine, or luminol.

9. The method of claim 8, wherein the at least one compound comprises 10-acetyl-3,7-dihydroxyphenoxazine.

10. The method of claim 1, wherein the at least one compound comprises phenol and 4-aminoantipyrine.

11. The method of claim 1, wherein measuring step (2) comprises measuring the fluorescence intensity of resorufin generated by reacting 10-acetyl-3,7-dihydroxyphenoxazine with $H_2O_2$ by peroxidase.

12. The kit of claim 4, wherein the compound that produces a compound with measurable fluorescence intensity, absorbance, or luminescence intensity by treatment with peroxidase in the presence of $H_2O_2$ is N,N'-bis(2-hydroxy-3-sulfopropyl)tolidine, 10-acetyl-3,7-dihydroxyphenoxazine, or luminol.

13. The kit of claim 12, wherein the compound that produces a compound with measurable fluorescence intensity, absorbance, or luminescence intensity by treatment with peroxidase in the presence of $H_2O_2$ is 10-acetyl-3,7-dihydroxyphenoxazine.

14. A kit for quantifying phosphatidylinositol containing phospholipase D, inositol dehydrogenase, NADH oxidase, and peroxidase, wherein each of the phospholipase D, inositol dehydrogenase, and NADH oxidase is independently derived from a microorganism, and the peroxidase is derived from a plant.

15. The method of claim 1, wherein the at least one compound is 10-acetyl-3,7-dihydroxyphenoxazine, and wherein the method comprises:
   a) treating the sample with phospholipase D, inositol dehydrogenase, and NADH oxidase to produce $H_2O_2$;
   b) reacting $H_2O_2$ produced in step a) with 10-acetyl-3,7-dihydroxyphenoxazine in the presence of peroxidase to produce resorufin; and c) measuring the fluorescence intensity of resorufin produced in step b) to quantify phosphatidylinositol in the sample using the calibration curve obtained beforehand.

* * * * *